United States Patent [19]

Bergner

[11] Patent Number: 4,562,829

[45] Date of Patent: Jan. 7, 1986

[54] STRONTIUM-RUBIDIUM INFUSION SYSTEM

[75] Inventor: Brian C. Bergner, Lawrenceville, N.J.

[73] Assignee: E. R. Squibb & Sons, Inc., Princeton, N.J.

[21] Appl. No.: 605,758

[22] Filed: May 1, 1984

[51] Int. Cl.[4] ............................................... A61N 5/52
[52] U.S. Cl. ...................................... 128/1.1; 128/655
[58] Field of Search .......................... 128/654, 659, 1.1

[56] References Cited

U.S. PATENT DOCUMENTS 4,202,345  5/1980  Farella ................................. 128/659

Primary Examiner—Peter D. Rosenberg
Attorney, Agent, or Firm—Lawrence S. Levinson; Sanford J. Asman

[57] ABSTRACT

The strontium-rubidium infusion system includes means for generating a solution containing rubidium-82, measuring the radioactivity in the solution, and infusing it into a patient in order to perform various studies on the patient's heart. The system includes a wash syringe which can be used by a physician to manually inject a bolus containing a large amount of radioactivity directly into a patient in order to perform first pass ventriculography studies.

12 Claims, 12 Drawing Figures

STRONTIUM-RUBIDIUM INFUSION SYSTEM

CROSS-REFERENCE TO RELATED APPLICATIONS

The present application is related to U.S. patent application Ser. No. 470,840 entitled DOSIMETRY SYSTEM STRONTIM-RUBIDIUM INFUSION PUMP, filed Feb. 28, 1983. It is also related to U.S. patent application entitled STRONTIUM-RUBIDIUM INFUSION PUMP WITH IN-LINE DOSIMETRY, filed by S. L. Barker and M. D. Loberg on Feb. 28, 1983.

BACKGROUND OF THE INVENTION

The present invention relates to a strontium-rubidium infusion system. In particular, it relates to a strontium-rubidium infusion system which has an in-line, real time dosimetry system which can be used to infuse patients with Rubidium-82, particularly for first pass ventriculography studies.

Current statistics show that approximately one-third of all deaths in the United States are related to coronary artery disease. See, for example, Pohost, G., McKusick, K., and Strauss, W., "Physiologic Basis and Utility of Myocardial Perfusion Imaging", Proceedings of the Second International Symposium on Radiopharmaceuticals, Society of Nuclear Medicine, New York 1979, pp. 465–473. This fact has prompted extensive research to more efficiently diagnose and manage this disease. Recent advances in radiopharmaceutical development and instrument design have established myocardial scintigraphy as an important new approach for evaluating coronary artery disease and myocardial perfusion. See, for example, Pierson, R., Friedman, M., Tansley, W., Castellana, F., Enlander, D., and Huang, P., "Cardiovascular Nuclear Medicine: An Overview", Sem. Nucl. Med., 9, 224–240 (1979); Leppo, J., Scheuer, J., Pohost, G., Freeman, L., and Strauss, H., "The Evaluation of Ischemic Heart Disease Thallium-201 with Comments on Radionuclide Angiography"; Sem. Nucl. Med., 10, 115–126 (1980); Vogel, R., "Quantitative Aspects of Myocardial Perfusion Imaging", Sem. Nucl. Med., 10, 146–156 (1980); Chervu, R., "Radiopharmaceuticals in Cardiovascular Nuclear Medicine", Sem. Nucl. Med., 9, 241–256 (1979); and Pitt, B., and Strauss, H., "Cardiovascular Nuclear Medicine", Sem. Nucl. Med., 7, 3–6 (1977).

Myocardial scintigraphy studies have been performed with several isotopes of potassium, rubidium, cesium, and thallium (Tl-201), although the usefulness of all of these nuclides is limited by their non-optimal physical properties. In spite of its long half-life and low-gamma energy, Tl-201 is currently the most widely used agent for myocardial imaging. See, for example, Poe, N., "Rationale and Radiopharmaceuticals for Myocardial Imaging", Sem. Nucl. Med., 7, 7–14 (1977); Strauss, H. and Pitt, B., "Thallium-201 as a Myocardial Imaging Agent", Sem. Nucl. Med., 7, 49–58 (1977); Botvinick, E., Dunn, R., Hattner, R., and Massie, B., "A Consideration of Factors Affecting the Diagnostic Accuracy of Tl-201 Myocardial Perfusion Scintigraphy in Detecting Coronary Artery Disease", Sem. Nucl. Med., 10, 157–167 (1980); and Wackers, F., "Thallium-201 Myocardial Scintigraphy in Acute Myocardial Infarction and Ischemia", Sem. Nucl. Med., 10, 127–145 (1980).

In diagnostic procedures in which the heart is involved, it is desirable for a diagnostician to be able to view a patient's heart. Heretofore, various radioactive materials have been used together with radiological procedures for viewing internal organs of patients. It has been difficult, however, to view a heart, because the radioactive substances which could be used for viewing the heart have had a very long half-life. Thus, using them with patients has involved an element of danger and each use reduces the number of times that a patient could be infused within any given time period. It would, therefore, be desirable to have a diagnostic apparatus and procedure which could be used with relative safety for viewing the heart.

Rubidium-82 is a potassium analog. That means it acts in a manner similar to potassium when it is infused into a patient. Thus it builds up at a very rapid rate, i.e., within seconds, in the patient's heart. Rubidium-82 also has the advantage of having a very short half-life, approximately 76 seconds. Therefore, it decays after a very short period of time following entry into the body, thereby allowing numerous procedures to be performed within a relatively short time period in a given patient. Rubidium-82 also has the advantage of being observable using a modified gamma camera, such as a gamma camera of the type manufactured by Searle Radiographics, Inc., called the PHO Gamma IV. A problem with using Rubidium-82 in a patient involves measuring the amount of radiation infused into the patient. In view of the very short half-life of Rubidium-82, it has heretofore been impractical to measure the radioactivity of a particular dose and to then infuse it into the patient using conventional means. An accurate method for measuring the amount of radiation being infused into the patient would be highly desirable for this particular application.

The availability of improved instrumentation has stimulated interest in the use of the positron emitter, Rubidium-82, for myocardial imaging. See, for example, Beller G., and Smith, T., "Radionuclide Techniques in the Assessment of Myocardial Ischemia and Infarction", Circulation, 53 (3, Supp. 1) 123–125 (1976); Budinger, T., Yano, Y., Derenzo, S., et al., "Myocardial Uptake of Rubidium-82 Using Positron Emission Tomography", J., Nucl. Med. 20, 603 (1979); Budinger, T., Yano, Y., Derenzo, S., et al., "Infarction Sizing and Myocardial Perfusion Measurements Using Rb-82 and Positron Emission Tomography", Amer. J. Cardiol., 45, 399 (1980). Rubidium-82, an analog of the alkali metal potassium, is rapidly cleared from the blood and concentrated by the myocardium. The short half-life of the Rubidium-82 (76 sec) offers the unique advantage of permitting repeat perfusion and blood flow studies in patients whose clinical status is rapidly changing.

Rubidium-82 is produced by the decay of its parent, strontium-82. E. R. Squibb and Sons, Inc. has developed a Rubidium-82 generator and infusion system which yields an isotonic saline solution of Rubidium-82 at physiological pH for rapid administration. In animal experiments, the safety and myocardial uptake of Rubidium-82 has been demonstrated. Therefore, this agent has been selected as a candidate for clinical trials.

In the patent applications identified above, a system for infusing Rubidium-82 into a patient while measuring the dose going into the patient was described. That system is useful in myocardial scintigraphy studies. In a modification to that system, described herein, a system which permits both myocardial scintigraphy studies, as well as first pass ventriculography studies, is described.

SUMMARY OF THE INVENTION

In accordance with the present invention, a strontium-rubidium infusion system is described. The system includes means for generating rubidium-82 in a solution which can be infused into a patient. In particular, the strontium-rubidium generator, described above, is typically used. Generated rubidium-82 is then collected in a piece of tubing having a predefined volume. This tubing is called the "dose volume" tubing, and it contains the dose volume of rubidium-82 solution which is to be infused.

The system also includes means for measuring the radioactivity present in the dose volume before the dose volume is infused into the patient and a wash syringe for quickly infusing the dose volume into the patient as a single bolus.

DETAILED DESCRIPTION OF THE PREFERRED EMBODIMENT

Figure 1:
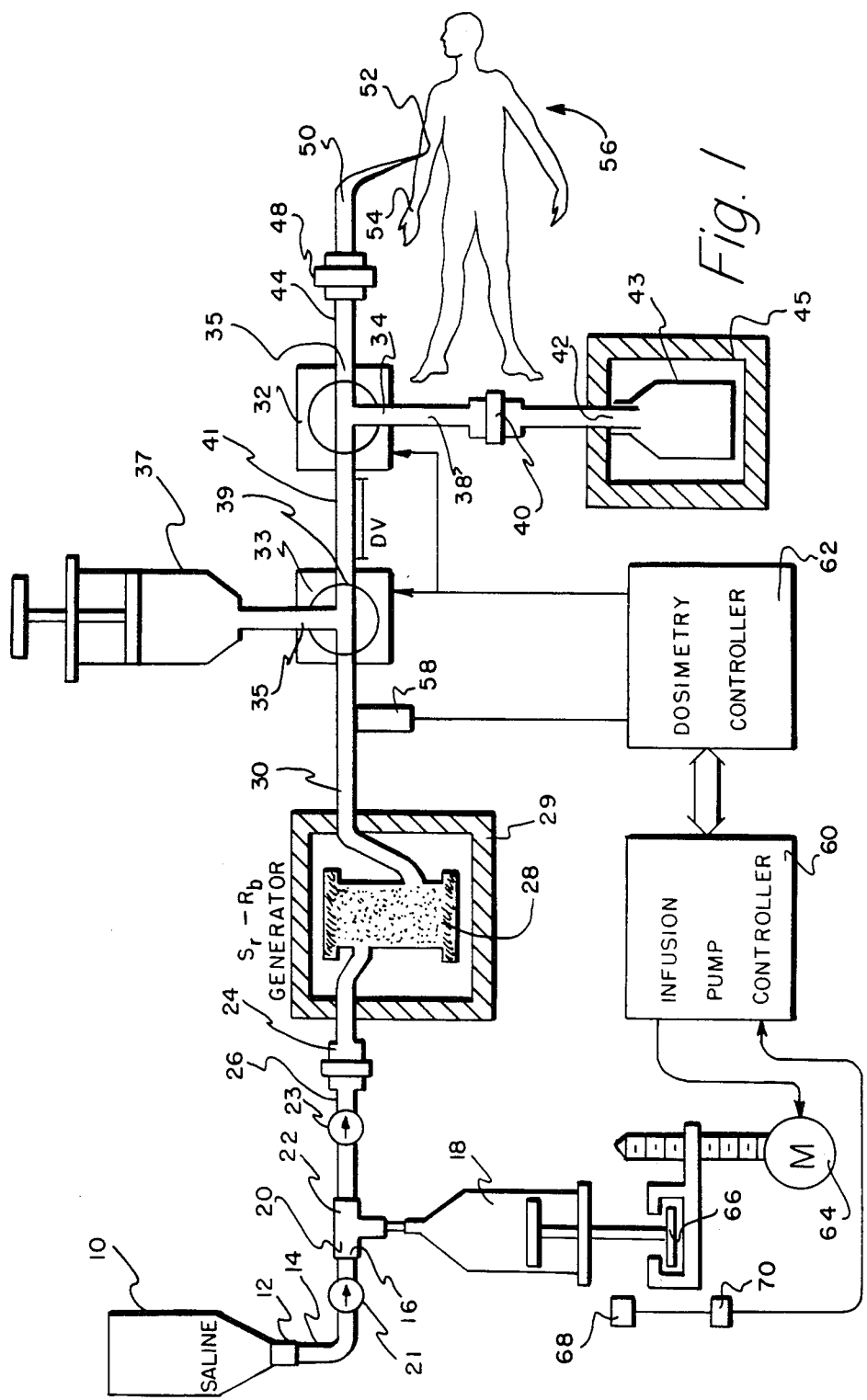
FIG. 1 is an overall schematic diagram of the strontium-rubidium infusion system of the present invention.

Referring now to FIG. 1, a saline bag 10 is connected, through a bullet nose fitting 12 and a piece of tubing 14, to a T-shaped two-way check valve 16 having three arms. A first arm 20 is attached to a one-way valve 21 which permits saline to enter the check valve 16, but does not allow it to exit back into the tubing 14. A second arm 22 includes a check valve 23 which permits saline to exit from the check valve 16 into a filter 24 through a tube 26, but does not allow it to re-enter the check valve 16 from the tube 26. An automatic syringe 18, connected to the check valve 16 fills from the saline bag 10 and pumps out through the tubing 26 into the filter 24. Saline pumped through the filter 24 enters a strontium-rubidium generator 28 which is of the type described more fully in U.S. patent application Ser. No. 156,285, entitled $^{82}$RB GENERATING METHOD AND ELUENT, filed on June 4, 1980 by Rudi D. Neirinckx, et al. The generator 28 is preferably enclosed in a lead shield 29.

Saline pumped through the strontium-rubidium generator 28 exits the generator 28 through tubing 30 containing Rubidium-82. The tubing 30 is connected to a diverter valve 33 having a first arm 35 which connects to a manually operated wash syringe 37. The remaining arm 39 is connected to a diverter valve 32 through a length of tubing 41 which is called the "dose volume" tubing 41, which has a length, DV. The length, DV, of the dose volume tubing, times its cross-sectional area, gives its volume, hereinafter referred to as the "dose volume".

Diverter valve 32 has a first arm 34 which leads through tubing 38, an antibacterial filter 40, through a tube 42, and ultimately to a waste collection container 43. The waste collection container 43 is preferably enclosed in a lead shield 45. A second arm 35 of the diverter valve 32 is connected through tubing 44, an antibacterial filter 48, additional tubing 50, and into an infusion needle 52. The infusion needle 52 is typically inserted into the arm 54 of a patient 56.

In the preferred embodiment of the invention, the check valve 16 is a dual back check valve of the type made by Beckton Dickenson Inc., and the antibacterial filters 24, 40, 48 are of the type made by Schleicher & Schull as their type FP030/3.

In the operation of the device to perform first pass ventriculography studies, the amount of radioactivity in the saline eluted from the strontium-rubidium generator 28 must be measured. Accordingly, a dosimetry probe 58 is placed adjacent to the tubing 30 where it measures the radioactivity of the rubidium-containing saline as it enters the the diverter valve 33. The diverter valve 33 is a three-part valve which permits flow from either the generator to the diverter valve 32 or from the wash syringe 37 to the diverter valve 32.

The diverter valves 32, 33 are connected to a dosimetry controller 62 for automatic operation. The operation of the dosimetry controller 62 will be further explained hereinafter. Based upon the signal sent by the dosimetry controller 62 to the valves 32, 33, the elution from the generator 28 is directed through the valves 32, 33 and the dose volume tubing 41 into the waste container 43 until such time as the minimum dose rate is met. Once the minimum dose rate for a first pass study has been reached, the dosimetry controller 62 starts integrating patient volume and dose to fill the dose volume tubing 41 with highly radioactive eluate. At that point, the valve 33 is switched to open the valve between the dose volume tubing 41 and the wash syringe 37 and close the valve leading through tubing 30 to the generator 28. Similarly, the diverter valve 32 is switched from the waste position to the patient position, and the physician performing the study quickly injects saline from the wash syringe 37 directly into the patient 56. That operation performs a number of different functions. In particular, it pushes the dose volume of radioactive eluate from the dose volume tubing 41 into the patient as a single highly radioactive bolus. Thereafter, the remaining saline in the wash syringe 37 clears the lines 41, 44, 50, purging them of radioactivity.

An advantage of the wash solution clearing the patient line of radioactivity is that the line does not "glow" in photos taken of the patient. Such a glowing interferes with data from the patient. An advantage of using the manually operated wash syringe 37 is that it allows a high infusion rate, on the order of 300 milliliters per minute, rather than about 50 milliliters per minute which can be obtained through automatic operation. The dose volume line 41 is typically of a length such that, together with its diameter, it holds between 3 and 10 ccs of fluid. Accordingly, it could be 3 to 4 feet long. Because of the length of the dose volume line 41, the dose volume line 41 can be placed within a standard dose calibrator of the type normally used in such studies. Accordingly, while the probe 58 and associated electronics are used to determine when to switch the divertor valves 32, 33 and while the electronics of the present device can also be used to measure the dose which is to be infused into the patient 56, a standard dose calibrator can also be used in first pass ventricularography applications.

As will be explained hereinafter, the present device can also be used in performing myocardial perfusion studies of the type described in the patent applications referred to earlier.

In order to use the infusion system, various procedures must be performed and controlled. In particular, the syringe 18 must be purged of air, and filled with saline, and the diverter valves 32, 33 must be positioned. These operations are contingent upon a number of factors including the total volume to be infused into the patient 56, the total dosage to be infused into the patient 56, the minimum radioactivity which must be present in the tubing 30 before any eluate is infused into the patient 56, the total volume to be infused (Note: The total volume eluted may differ from the total volume infused into the patient 56 as some volume is likely to be diverted to waste.).

Figure 2:
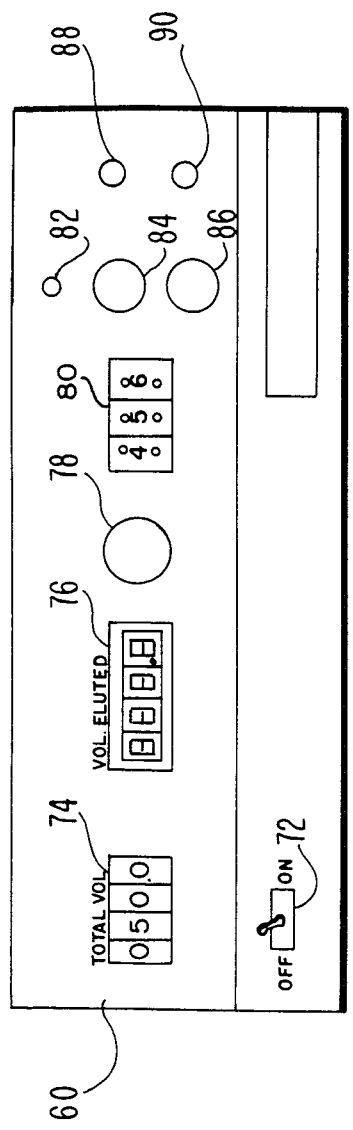
FIG. 2 is a front view of the infusion pump control used with the strontium-rubidium infusion system.
Figure 3:
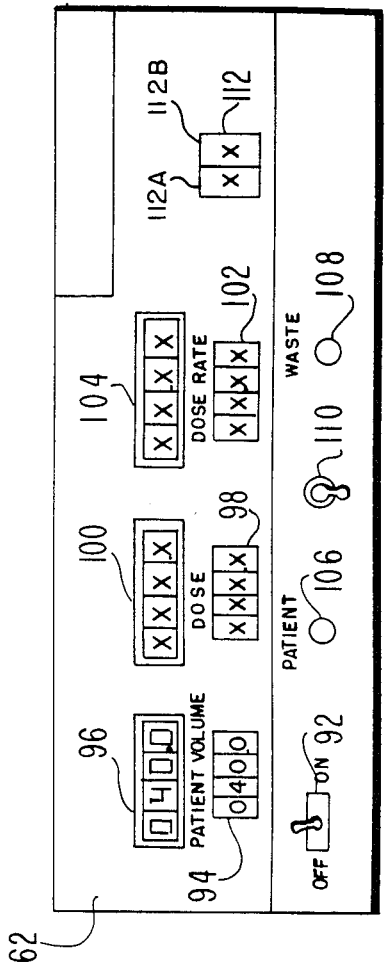
FIG. 3 is a front view of the dosimetry control used with the strontium-rubidium infusion system.

The foregoing parameters may be altered from the front panel of two different controllers shown in FIGS. 2 and 3. These are the infusion pump controller 60 and the dosimetry controller 62, repectively. The infusion pump controller 60 controls the mechanical movement of the syringe's plunger 66 via a stepping motor 64 which is connected to the plunger 66.

In the preferred embodiment of the invention, the syringe 18 is a sterile, disposable plastic syringe of the type made by Sherwood Medical and designated as Part. No. 881-514031. The infusion pump controller 60 limits the movement of the syringe plunger 66 based upon optical limit detectors 68, 70 which limit the fully displaced and fully extended positions of the plunger 66, respectively. The volume control function performed by the infusion pump controller 60 is accomplished by counting the number of pulses sent to the stepping motor 64.

With reference to FIG. 2, the front panel of the infusion pump controller 60 is shown. The infusion pump controller 60 includes an on/off power switch 72 which is used to turn on the power to the unit.

A set of thumbwheel switches 74 is used to select the total volume (ml) to be eluted. An LED display 76 shows the total volume (ml) which has been eluted. A momentary contact push-button switch 78 is used to start and to stop the movement of the plunger 66 in the forward (inject) direction.

A set of push-button potentiometers comprise the Flow Rate Control 80 which is used to determine the volume per unit time which is infused. The Flow Rate Control 80 sets the pulse rate into the stepping motor 64. An LED 82 lights when the end of travel of the plunger 66, as indicated by the optical limit detectors 68, 70 is reached. A pair of momentary contact push-button switches 84, 86 are used to control the purge and refill functions, respectively, of the syringe 18. Thus, if the purge control switch 84 is pushed, and held, the plunger 66 continues to move in the forward direction until it reaches the forward limit detector 68. Similarly, while the refill control switch 84 is pressed and held, the plunger 66 continues to move toward the rear limit detector 70. The speed of movement of the plunger 66 during purge and refill operations are controlled by adjustable screw-type potentiometers 88, 90, respectively.

The infusion pump controller 60 is comprised of a Superior Electric Company STM103 Translator Module which is interfaced to provide signals representative of flow rate, volume eluted, and injection. It is also interfaced to be remotely controlled. A pulse called "INIT" indicates that the Translator Module has been powered. The "INIT" pulse is used to reset the displays on the dosimetry module. An "INJECT" signal indicates that the pump is injecting. Output pulses, corresponding to 0.1 ml steps of the syringe 18, are provided. An "End of Elution" signal is used to remotely disable the infusion pump controller 60.

With reference now to FIG. 3, the dosimetry controller 62, is comprised of a number of LED displays and thumbwheel switch sets. In addition, the dosimetry controller 62 includes an on/off switch 92 for providing power to the unit.

The first set of thumbwheel switches 94 is used to set the volume (ml) to be infused into the patient 56. The LED display 96, immediately above the thumbwheel switches 94, displays the volume of eluate which has been infused into the patient 56.

The thumbwheel switches 98 are used to set the total dose (mCi) which is to be infused into the patent 56 and the LED display 100 immediately above the total dose thumbwheel switches 98 displays the total dose which has been infused into the patient 56. Similarly, the thumbwheel switches 102 are used to set the dose rate (mCi/sec.) which is to be used to determine when to switch the diverter valve 32 from the waste position to the patient 56 position. The actual dose rate which is present in the eluate within the tube 30 in front of the dosimetry probe 58 is displayed on the LED display 104. The description of the dose present in the eluate at any given time from the start of infusion will be provided hereafter. The dosimetry controller 62 further comprises a pair of LED's 106, 108 which indicate the position of the diverter valves 32, 33. Only one of these two LED's 106, 108, should be on at any given time.

While the normal position of the diverter valves 32, 33 is toward waste from the generator 28, except when eluate is being manually infused into a patient 56, provision must be made to clear the tubing 44, 50 of any air prior to infusing a patient 56. Accordingly, the dosimetry controller 62 includes a toggle switch 110 which is used to hard wire the diverter valve 32 in the patient 56 position.

The present preferred embodiment of the invention also includes a set of thumbwheel switches 112 which are used to set the flow rate which will be used in internal calculations of dosimetry controller 62. It is presently anticipated by the inventor that a future version of the present invention will include automatic means for determining the flow rate based upon the settings used in the infusion pump controller 60.

Figure 4:
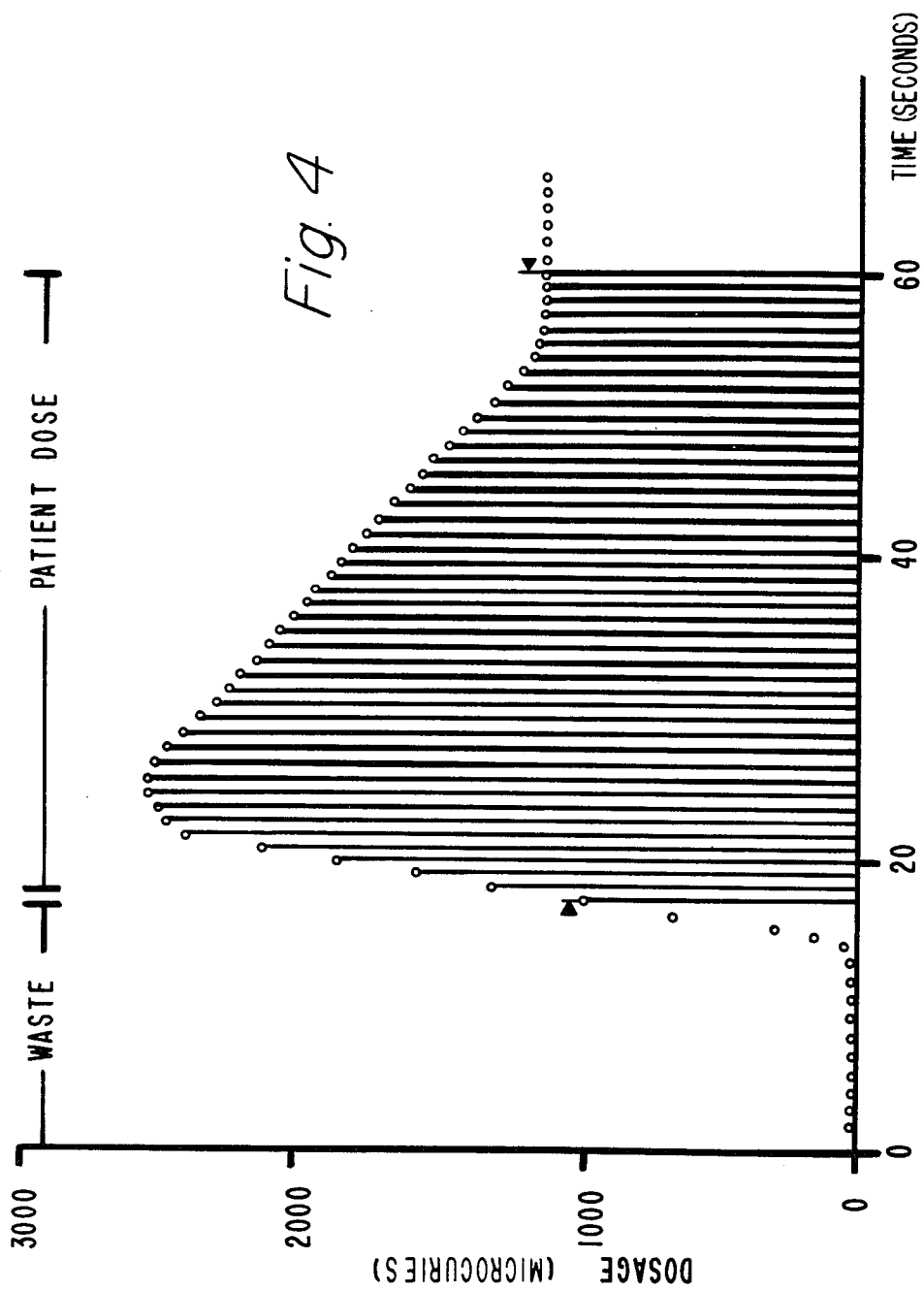
FIG. 4 is a graph of radioactivity measured (on the y-axis) by the dosimeter probe versus time (on the x-axis)

Referring now to FIG. 4, a graph of the radioactive dosage present in the tubing 30 in front of the dosimetry probe 58, is shown. In the graph, the dosage is measured on the y-axis and time is measured on the x-axis. The time is referenced with zero being the time that the start/stop inject button 78 on the infusion controller 60 is pushed to commence infusion.

For approximately 10 seconds there will be no radioactivity present in the eluate from the strontium-rubidium generator 28. Thereafter, the dose rate rises at a rapid rate up to a maximum, after which the dose rate falls to a level value indicative of the steady state regeneration rate of the Sr-Rb generator 28. Thus, when the infusion starts, there is a delay initially as the dose rate builds up, a reduction in dosage after the generator 28 is partially eluted, and then there is a dosage representative of the steady state regeneration rate of the generator 28.

The setting of the dose rate thumbwheel switches 102 tells the dosimetry controller 62 at what point along the upward slope of the dosage curve to start integrating the patient volume (i.e., the volume in dose volume line 41 which will be infused into the patient 56) and the patient dose. At that point the dose indicated by the LED's 100 will start accumulating from zero, where it had been until that point. Similarly, the patient 56 volume indicated by the LED's 96 will start to accumulate as of that time.

Once highly radioactive eluate is infused into the dose volume line 41 it continues to be infused until one of various stop indications occurs. In particular, when the total patient 56 dose, set by the thumbwheel switches 98, is reached, the diverter valve 32 is opened to the patient position, diverter valve 33 is closed from the generator 28 and opened to the wash syringe 37, and the stepping motor 64 stops, thereby preventing further infusion. Similarly, the diverter valves 32, 33 are switched, and the stepping motor 64 is stopped when the patient volume 96, preset by the thumbwheel switches 94 reaches its preset value or after the total volume to be eluted, set by the volume thumbwheel switches 74 reaches its preset value; or when the purge limit optical stop 68 of the syringe 18 is reached; or if the start/stop inject button 78 is pushed. Any of the foregoing events causes the diverter valves 32, 33 to switch, and causes the stepping motor 64 to stop. Note, however, that the purge and refill switches 84, 86 are disabled as of the time that the start/stop inject button 78 is pushed to commence the infusion.

Quantizing Radioactivity in a Liquid Stream

In order to measure the radioactivity in the saline solution which passes through the line 30 in front of the dosimetry probe 58, it is necessary to count the number of disintegrations which occur in front of the probe 58, while at the same time keeping track of the flow rate of the saline through the tube 30. Given that these quantities are known, it is possible to measure the total activity in milliCuries (mCi) in accordance with the following formula:

$$A = [(C)(F)]/[(V)(E)(CM)(Y)]$$

Where,
A = total activity (mCi);
C = net counts;
F = flow rate (ml/min);
V = volume in detector view (ml);
E = net efficiency (counts per minute/disintegration per minute);
CM = disintegrations/minute to milliCurie conversion factor; and
Y = net yield of photon.

In the case of the present invention, the above formula can be simplified to:

$$A = [(C)(F)]/K$$

Where,
A = total activity (in milliCuries);
C = net counts (from probe);
F = the flow rate; and
K = the calibration factor.

As noted, the calibration factor, K, takes into account the volume in the detector's view, the net efficiency of the probe, the conversion factor in terms of disintigrations per minute to milliCuries, and the net yield of photons. These factors are substantially constant for any given probe and tubing combination for a reasonable amount of time. Accordingly, provision is made on the circuit board to adjust the calibration factor, K, when the instrument is serviced. However, the calibration factor, K, is not user adjustable in the normal course of operation.

Dosimetry Probe

Figure 5:
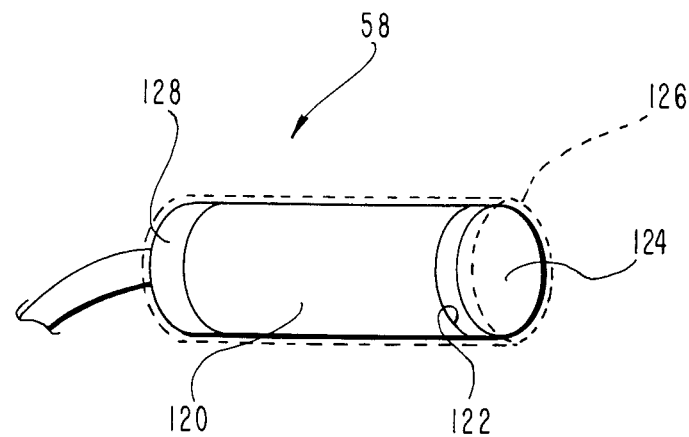
FIG. 5 is a perspective view of the dosimetry probe.

Referring now to FIG. 5, the dosimetry probe 58 is comprised of a photomultiplier tube 120, such as the RCA C83009E 14 mm diameter 10-stage photomultiplier tube manufactured by the Electro Optics Division of RCA Corporation in Lancaster, Pa. The photomultiplier tube 120 has a face 122 through which input signals in the form of light are received. On the face 122, a plastic scintillator 124, such as a Nuclear Enterprises Type 102A manufactured in Edinburgh, Scotland, is mounted. In the preferred embodiment of the invention, the plastic scintillator 124 is glued or bonded to the face 122 of the photomultiplier tube 120. After the plastic scintillator 124 has been bonded to the face 122 of the photomultiplier tube 120, an aluminum foil covering (not shown) is placed over the face end of the photomultiplier tube 120, including the plastic scintillator 124. The purpose of the aluminum foil covering is to reflect back into the tube 120 any light which scintillates from the plastic scintillator 124 away from the tube 120. In addition, the aluminum foil covering prevents any stray light which might come into the area of the face 122 from getting into the tube 120. Following the application of the aluminum foil, a light tight material, such as black electrical tape is wrapped over the aluminum foil covered tube 120 in order to further prevent any light from entering into the tube 120. The tape-wrapped tube 120 is then inserted into a mu metal shield 126 which is intended to prevent any electromagnetic radiation effects from affecting the output of the dosimetry probe 58. In the preferred embodiment of the invention, the dosimetry probe 58 is plugged into a standard photomultiplier tube socket base 128 containing a standard resistive biasing network.

Dosimetry Circuitry

Figure 6:
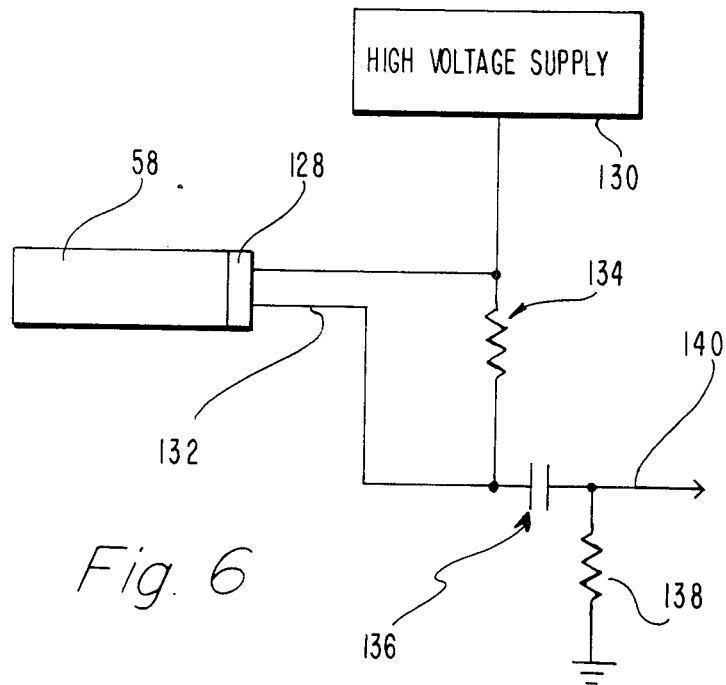
FIG. 6 is a schematic diagram of the interface between the dosimetry probe of FIG. 4 and the dosimetry control circuitry.

Referring now to FIG. 6, the photomultiplier tube socket base 128 includes a resistive network containing biasing resistors for placing appropriate bias voltages on the ten dynodes in the photomultiplier tube 120. Accordingly, the high voltage connection to the photomultiplier tube base 128 is automatically biased to provide appropriate operating voltages to the photomultiplier tube 120. The high voltage supply 130 used in the preferred embodiment of the invention is a 0–1000 volt, adjustable Bertan PMT-10A-P power supply manufactured by Bertan Associates, Inc., Three Aerial Way, Syosset, N.Y. In the present application, the high voltage supply 130 is adjusted to provide an output voltage of 950 volts. The photomultipler tube socket base 128 is an RCA photomultipler tube socket base, Part No. AJ2273.

An output signal goes from the dosimetry probe 58 on a line 132 to a coupling network comprising a pull up resistor 134, a coupling capacitor 136, and a output resistor 138. Accordingly, an AC signal having a peak to peak maximum of approximately 250 millivolts with negative going pulses, is provided on output line 140.

Single Channel Analyzer

Figure 7:
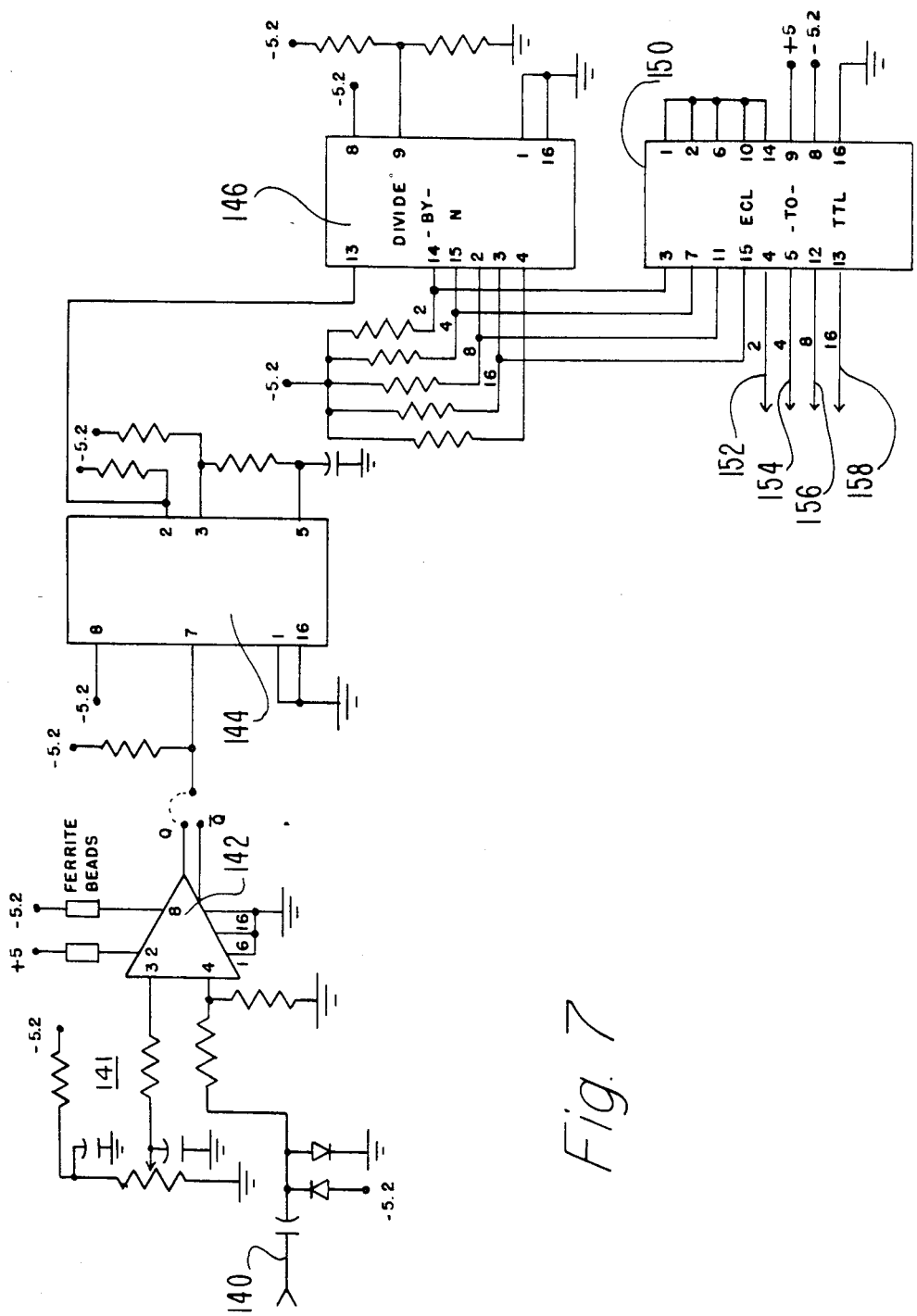
FIG. 7 is a schematic diagram of the circuit for the Single Channel Analyzer used to convert and shape the raw pulses from the dosimetry probe of FIG. 4.

Referring now to FIG. 7, the schematic diagram for a Single Channel Analyzer circuit is shown. The Single Channel Analyzer is used, because the pulses on output line 140 from the Dosimetry circuitry are very sharply defined pulses which may occur at very high frequencies. In view of the fact that it is important to count all the pulses, a very high speed comparator, such as an AM685 voltage comparator 142, manufactured by Advanced Micro Devices, 901 Thompson Place, Sunnyvale, Calif., with emitter-coupled logic (ECL) output, or other suitable very high speed comparator, must be used.

A biasing network 141 consisting of a series of resistors and capacitors is used as one input to the comparator 142. In view of the fact that the pulses which are handled by the comparator 142 are of very short duration, a one-shot circuit 144, comprised in the preferred embodiment of the invention, of a Motorola type 1670 master-slave flip-flop integrated circuit, is used to stretch the pulse width up to a uniform pulse width of approximately 50 nanoseconds. The output signal from the one-shot 144 is fed into a programmable divide-by-N circuit 146, which in the preferred embodiment of the invention is comprised of a Motorola Type 10136 universal hexadecimal counter integrated circuit. The divide-by-N circuit 146 is programmable. Accordingly, a very high pulse repetition rate coming into the comparator with very short pulse widths is reformed by the one-shot to have wider, uniform pulses, and the input signal is further reformed by the divide-by-N circuit to bring the pulse repetition rate down into any desirable range. In particular, outputs of the divide-by-N circuit 146 are provided for N equal to 2, 4, 8, and 16.

Up through this point in the circuit, the devices have all been of ECL type in order to be able to handle the very high speed pulses which are detected by the dosimetry probe 58. In view of the fact that it is conventional to use transistor-transistor-logic (TTL) integrated circuits, a type 10125 ECL-to-TTL level converter circuit 150 is hooked to the output of the divide-by-N circuit 146. Thus, the ECL-to-TTL level converter circuit 150 transforms the ECL signal levels into TTL signal levels for further processing. The TTL outputs leave the ECL-to-TTL level converter circuit 150 on four lines 152, 154, 156, 158, which correspond to the TTL level of the counts into the Single Channel Analyzer divided by 2, 4, 8, and 16, respectively. The counts out on the lines 152–158 will be referred to hereafter as the "net counts".

Multiplier-Divider Circuit

Figure 8:
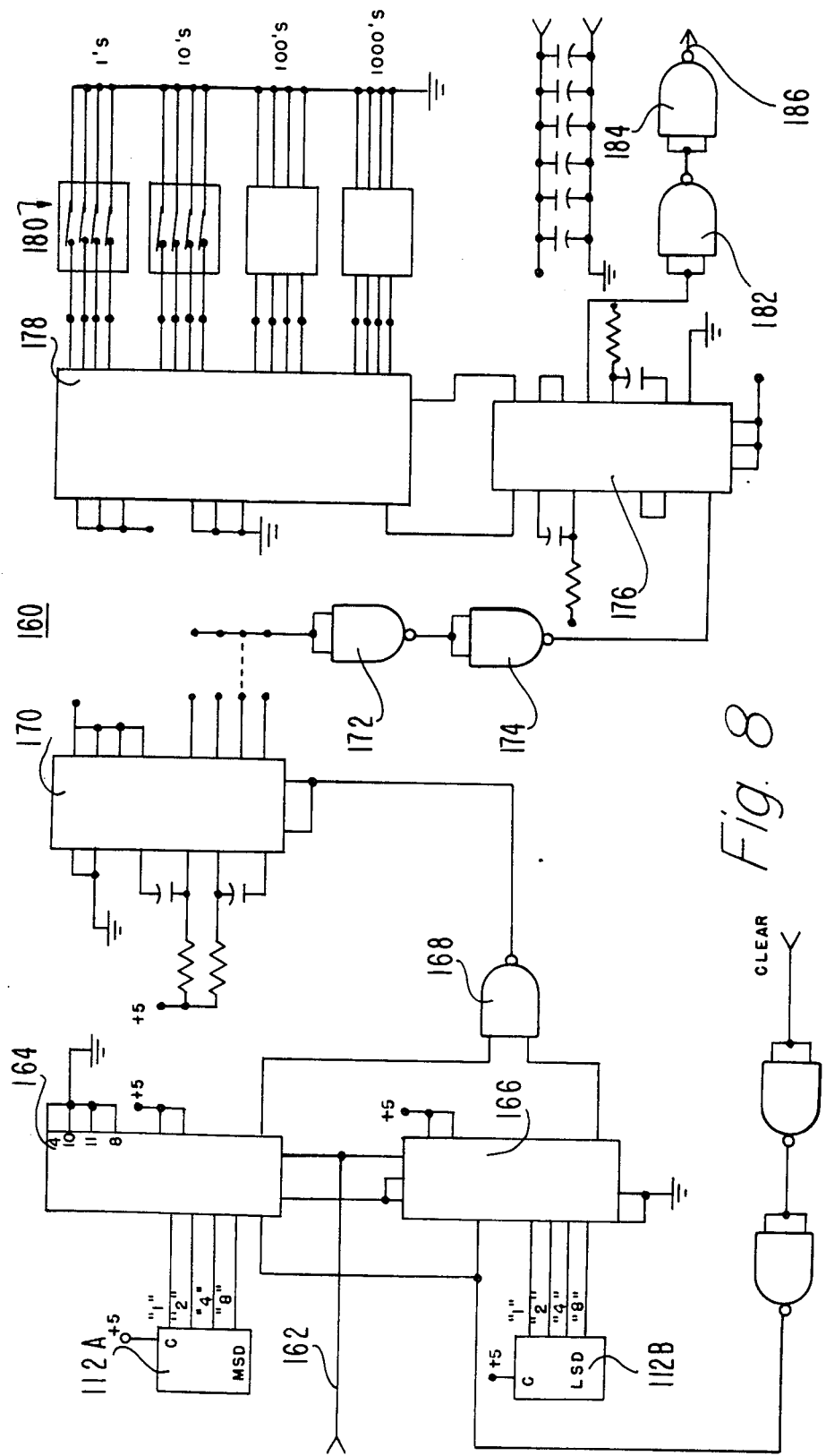
FIG. 8 is a schematic diagram of the circuit for the Multiply-Divide circuit used to carry out the formula which converts pulses from the Single Channel Analyzer into radioactivity present in front of the dosimetry probe.

Referring now to FIG. 8, there is a Multiplier-Divider circuit 160 which converts the net counts from the Single Channel Analyzer circuit, described above, into a meaningful quantity (milliCuries). The Multiplier-Divider circuit 160 accepts the "net counts" on an input line 162 which is connected to one of the lines 152–158 from the Single Channel Analyzer (i.e., the raw counts converted into TTL levels and then divided by 2, 4, 8, or 16) and multiplies them by the eluate Flow Rate divided by 100. The result is then divided by a constant, K, in order to carry out the formula:

$$A = [(N)(F)]/K$$

Where,
A = total activity (in milliCuries);
N = net counts (from Single Channel Analyzer);
F = Flow Rate; and
K = the calibration factor.

The net counts, N, are first multiplied by a two digit number corresponding to the eluate Flow Rate (entered on the Flow Rate thumbwheel switches 112A, 112B, corresponding to the most significant digit (MSD) and the least significant digit (LSD), respectively, the thumbwheel switches 112A, 112B are on the front panel of the dosimetry controller 62, shown in FIG. 3. The multiplication is accomplished by cascading two TTL Synchronous Decade Rate Multiplier circuits (F74167), and sending their outputs through a NAND gate 168. The resulting output corresponds to $F_{out}$, where:

$$F_{out} = [(N)(F)]/100$$

The output pulses are of varying duration, so they are next fed through a pair of one-shots which process them to have a fixed duration. In the preferred embodiment of the invention, the first one-shot is comprised of one-half of an SN74123 integrated circuit 170. The first one-shot is negative edge triggered, and it provides a pulse output of approximately 200 nanoseconds. Its output is double buffered through buffers 172, 174 into a second one-shot which is comprised of one-half of a CD4098BE integrated circuit 176 in order to increase the width of the output pulses, so they will be acceptable to a CMOS divider integrated circuit 178. The second one-shot is configured to be leading edge triggered.

The output of the second one-shot is then divided by the calibration factor, K, which may have a range of between 3 and 9,999. A CD4059A integrated circuit 178 is used as a programmable divide-by-N counter. Programming is accomplished via a series of 16 DIP switches 180 mounted on the printed circuit card. Each set of four switches corresponds to the BCD settings for 1's, 10's, 100's and 1000's. Pull up resistors (not shown) are employed in the standard manner so that when the DIP switches are open the inputs to the divide-by-N circuit 178 are pulled high.

The output of the divider 178 has pulses of random widths, so another one-shot, made up of the second half of the CD4098BE 176 configured for leading edge triggering, is used. This one-shot provides an output pulse duration of approximately 20 microseconds. Before leaving the Multiplier-Divider circuit 160, the output is double buffered through buffers 182, 184 and the output signal on line 186 is sent to the Dose Rate circuit. There will be one dose corrected output pulse on line 186 for each 0.01 milliCurie of activity which passes by the dosimetry probe 58.

Display Controller Circuit

Figure 9:
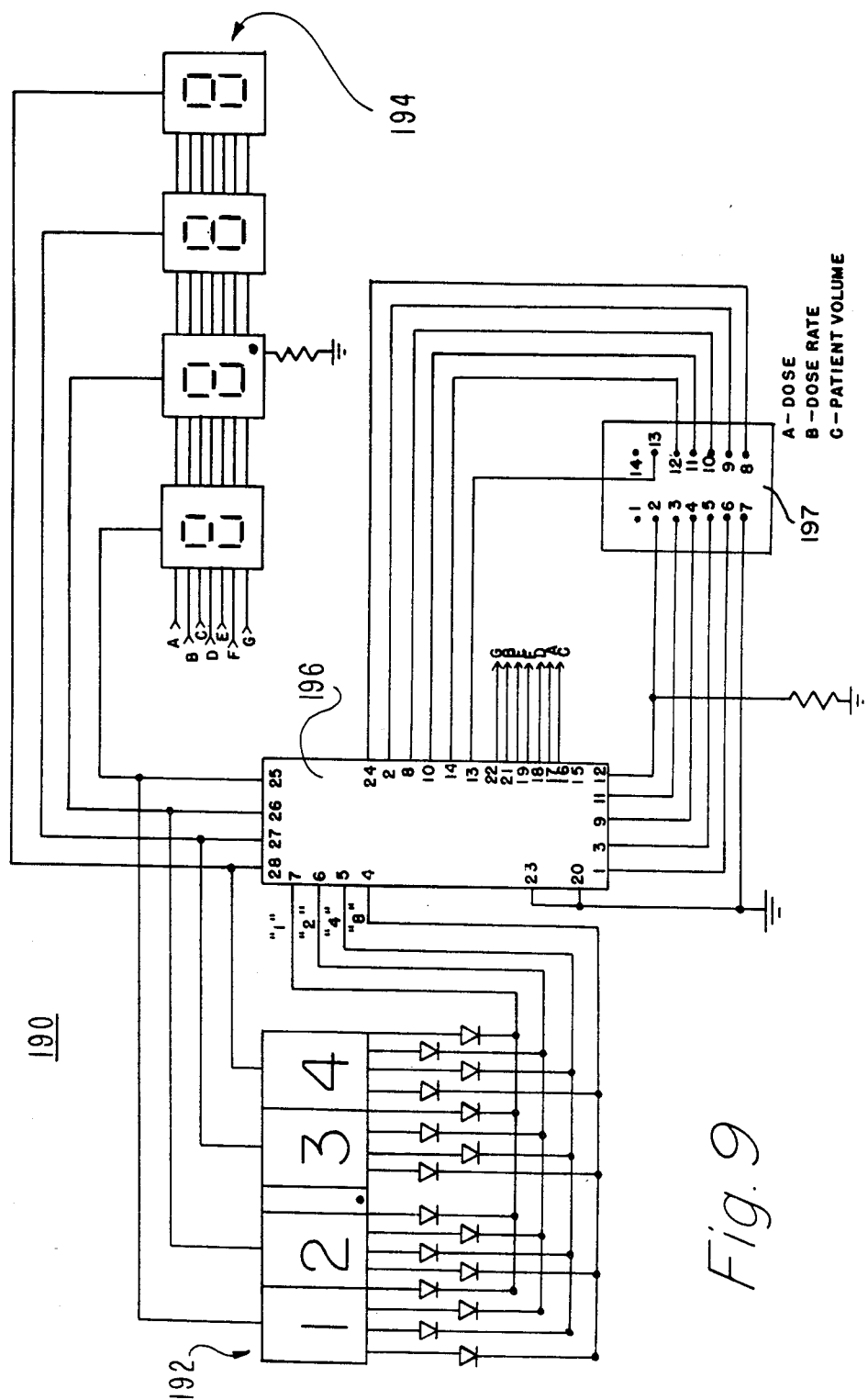
FIG. 9 is a schematic diagram of one of the Display Controller circuits used to interface the switches and the displays to the other circuitry.

Referring now to FIG. 9, the schematic diagram for a Display Controller Circuit 190 is shown. There are three Display Controller Circuits within the dosimetry controller 62. Each Display Controller 190 is used both to interface a set of thumbwheel switches 192 and to display the quantity associated with the particular set of thumbwheel switches 192. Thus, there is one Display Controller of 190 for Dose Rate (which works with thumbwheel switches 102 and LEDs 104), one for Patient Volume (which works with thumbwheel switches 94 and LEDs 96), and one for Dose (which works with thumbwheel switches 98 and LEDs 100). Each Display Controller Circuit 190 drives four seven-segment displays 194, such as MAN71 displays.

The major component of the Display Controller Circuit 190 of the preferred embodiment of the invention is an Intersil ICM7217IJI integrated circuit 196, which is a device which provides a direct interface to the seven-segment displays 194. Each Display Controller Circuit 190 allows the user to set a level, by programming binary coded decimal (BCD) thumbwheel switches 192. The levels can then be detected. In this way, a preset limit for Dose, for example, will be detected and will be used to shut down the infusion pump. For Dose Rate, the preset level is used to switch the position of the diverter valve 32, through the valve driver circuit which will be explained hereinafter. The Patient Volume can also be preset, and the infusion pump can be stopped at the preset limit.

Dose Rate Circuit

Figure 10:
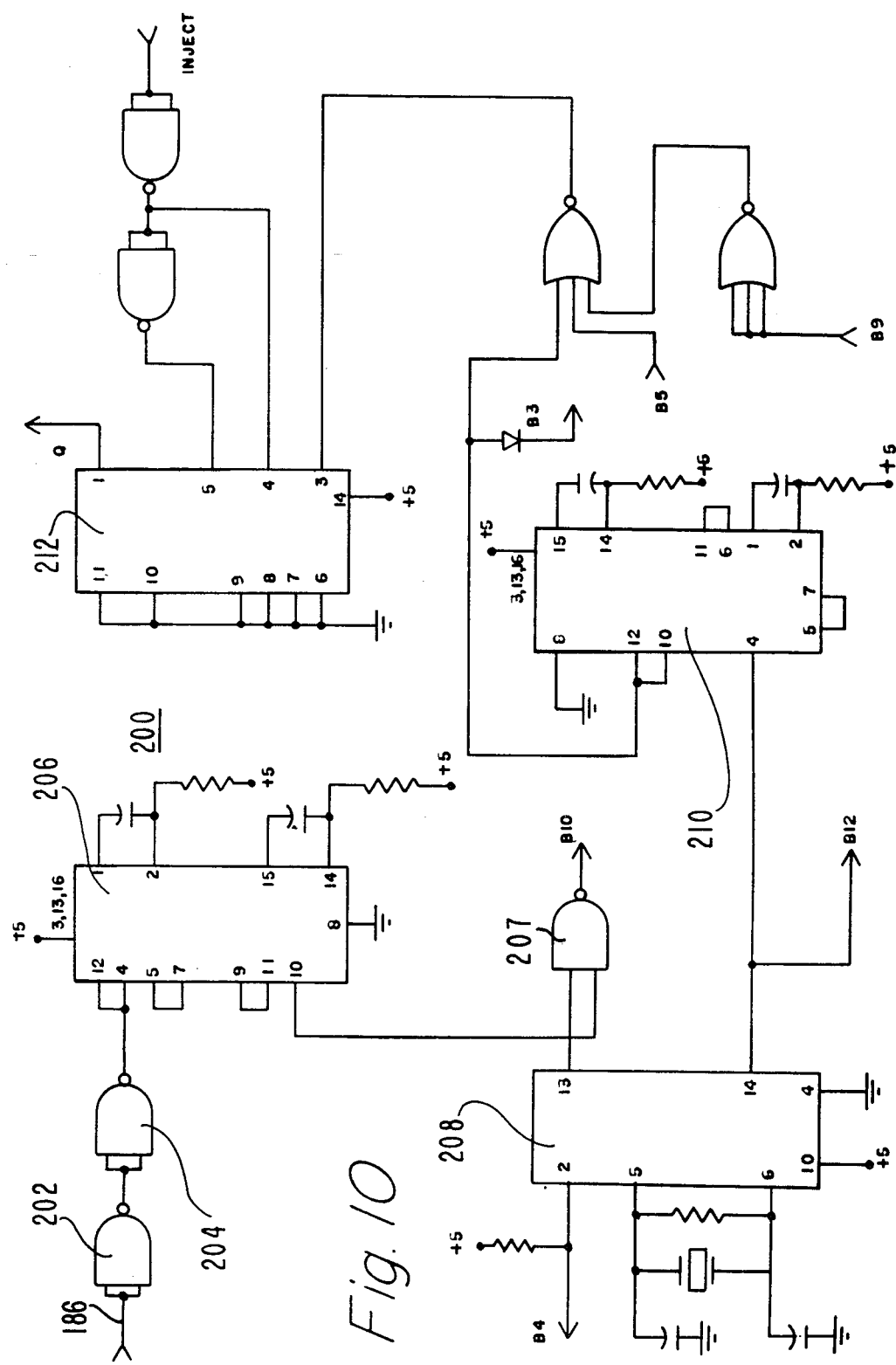
FIG. 10 is a schematic diagram of the Dose Rate circuit used to provide a display of the amount of radiation present in the eluate.

The Dose Rate circuit 200, shown in FIG. 10, provides a visual display of the amount of radiation present in the eluate. The Dose Rate circuit 200 employs a Display Controller Circuit, of the type described above. The Dose Rate display is constantly updated to provide the user with Dose Rate information. The Dose Rate circuit 200, with the Display Controller, is programmed to set a trigger level for switching the eluate from waste to the patient 56.

The Dose Rate circuit 200 uses signals from the Multiplier-Divider circuit 160, described above, and from the Control Board which will be described hereinafter. The dose corrected output pulses on line 186 from the Multiplier-Divider circuit 160 described above (i.e., 1 pulse/0.01/mCi) enter the Dose Rate circuit 200, and are double buffered by buffers 202, 204. The buffered pulses are then fed through one-half of a one-shot 206, comprised of a CD4098BE integrated circuit in the preferred embodiment of the invention. The output from the one-shot 206 is gated through NAND gate 207 to the Dose Rate Display 104 since there are three Display Controller Circuits 190, which are used for Dose (circuit "A"), Dose Rate (circuit "B"), and Patient Volume (circuit "C"), the designation "B10" at the output of NAND gate 207 means pin 10 on input connector 197 (see FIG. 9).

The heart of the Dose Rate circuit 200 is an Intersil ICM7207A Oscillator Controller integrated circuit 208. This unit, along with a dual one-shot comprised of a CD4098BE integrated circuit 210, in the preferred embodiment of the invention, provides all of the control necessary for gating, storing, and resetting the display.

The outputs of the Dose Rate Display Controller Circuit provide an easy interface to determine when a predetermined count (corresponding to the dose rate which was set on thumbwheel switches 102) has been reached, and to generate a signal which is used to enable the Dose and Patient Volume Displays, 100, 96, respectively.

In the preferred embodiment of the invention, the signal utilized to enable the Dose and Patient Volume Displays 100, 96, respectively, is derived from one half of a dual D-type flip-flop, such as a CD4013BE integrated circuit 212. The flip-flop 212 is only enabled during an injection. The enabling "INJECT" signal is generated when the pump is injecting. Once an injection is started and a user pre-set Dose Rate limit set on thumbwheel switches 102 is met, the flip-flop 212 latches a positive Q output to enable the Dose Display and the Patient Volume Display.

Control Circuit

Figure 11:
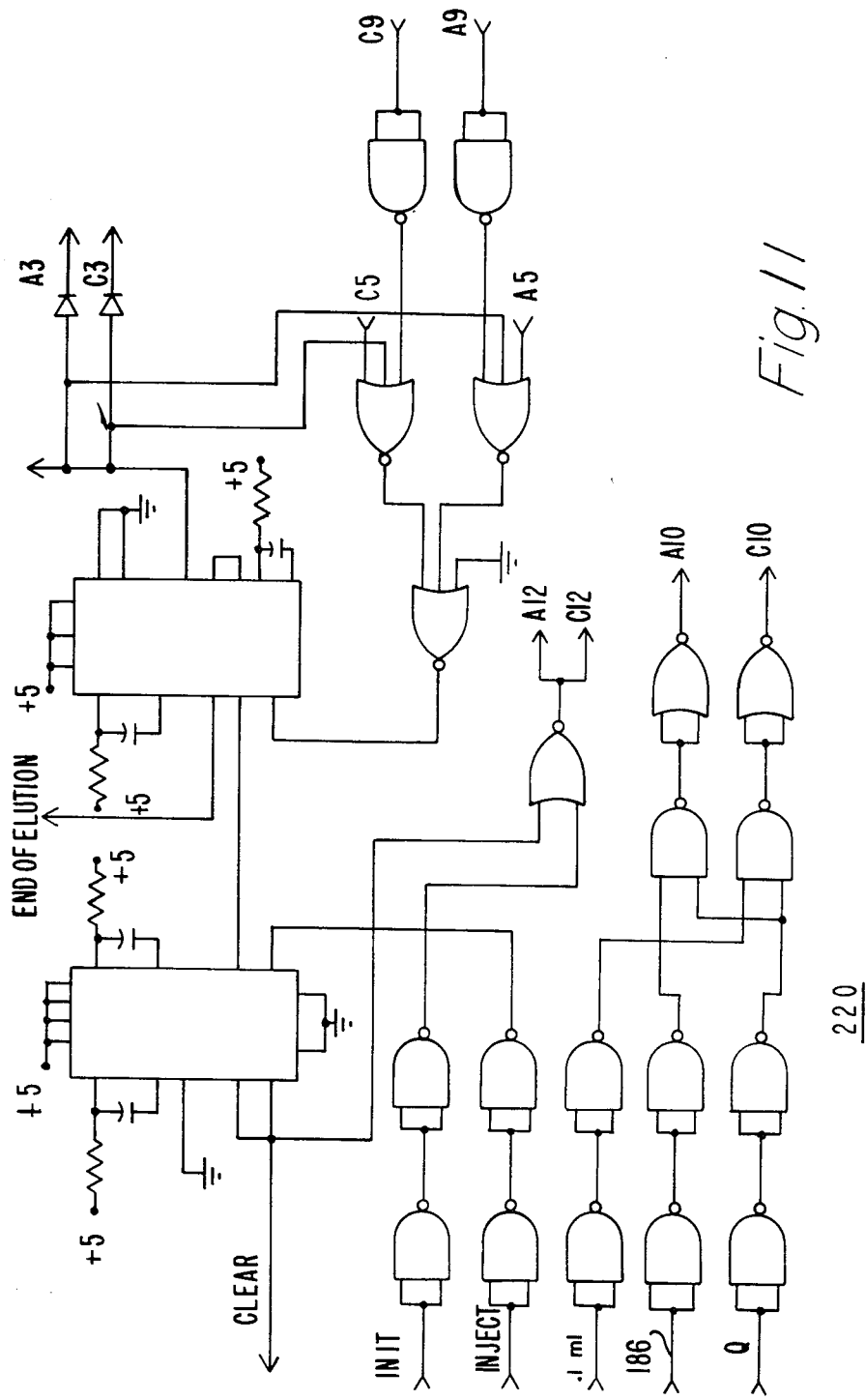
FIG. 11 is a schematic diagram of the Control Circuit which oversees the operation of the remainder of the circuitry.

Referring now to FIG. 11, the schematic diagram of the Control circuit 220 is shown. The purpose of the Control circuit 220 is to "oversee" all other operations. Specifically, the Control circuit 220 controls the Dose Display and Patient Volume Display. The Control circuit 220 also provides timing for resetting the Multiplier-Divider circuit 160, and it buffers various inputs and outputs to and from the infusion pump control module 60.

The basic function for turning the infusion pump off is the End of Elution signal. The End of Elution signal is derived from either the Dose Display 100 or the Patient Volume Display 96. These displays 100, 96 are gated to begin counting once the Dose Rate trigger level, the Q output from flip-flop 212, reaches its preset limit, as defined by the Dose Rate thumbwheel switches 102. Then, once the Dose or Patient Volume is met, as defined by the Dose thumbwheel switches 98 and by the Patient Volume thumbwheel switches 94, respectively, the Control circuit 220 signals the pump to stop.

Valve Driver Circuit

Figure 12:
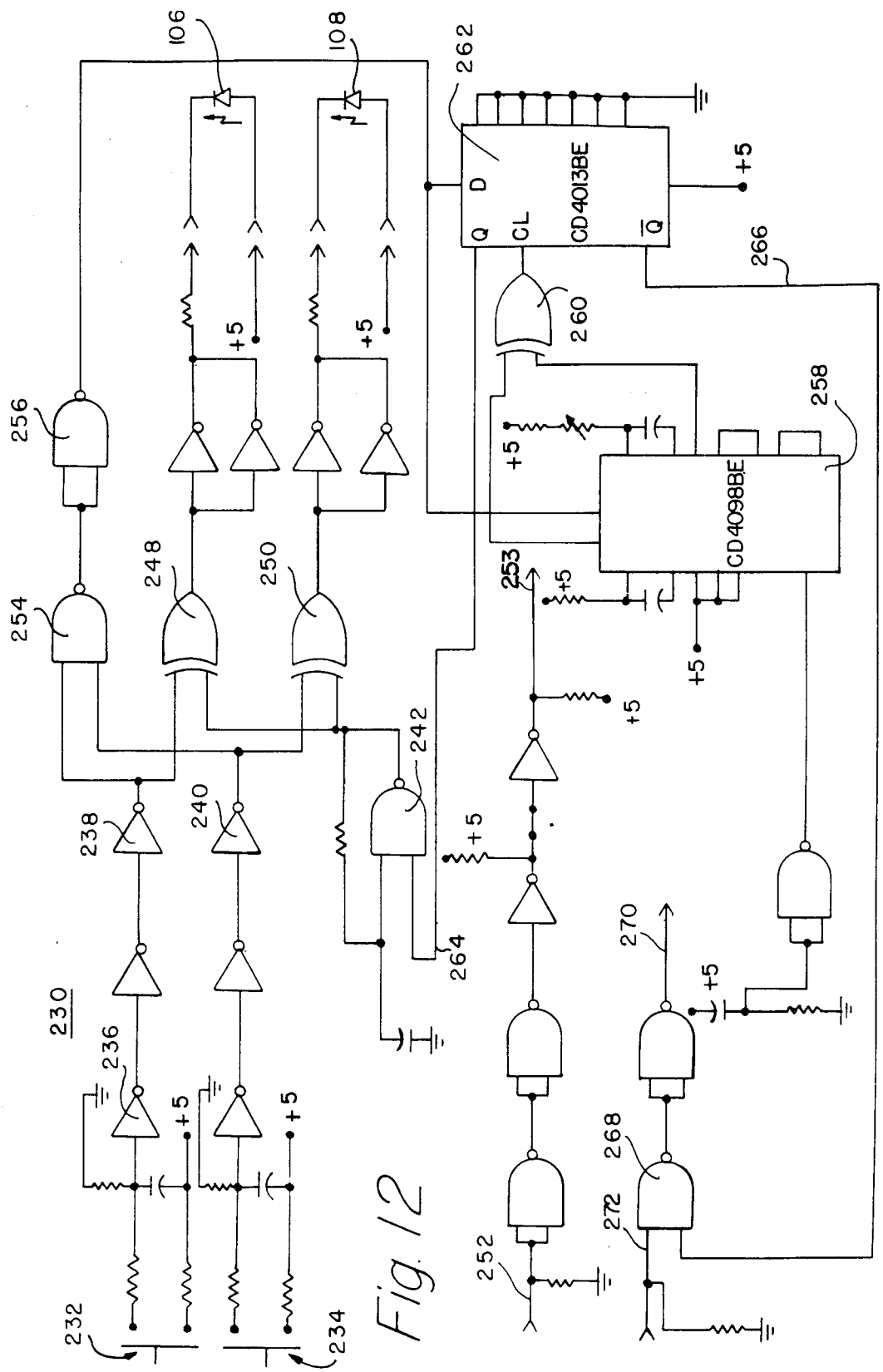
FIG. 12 is a schematic diagram of a valve driver circuit.

The Valve Driver circuit 230, shown schematically in FIG. 12, is used to control the switching of the diverter valves 32, 33 which direct the eluate either to the patient 56 or to waste. The Valve Driver circuit 230 accepts its input from the infusion pump controller or from the Patient Line Purge Switch 110. The Patient Line Purge Switch 110 directly controls the valves 32, 33.

The diverter valves 32, 33 are two position valves which include electrical switches which close individually when the valves 32, 33 are fully in one of their two positions, i.e., either the patient or waste position for valve 32. Movement of the valves 32, 33 from one position to the other is controlled by an AC motor which includes two windings. When the first winding is energized, the motor moves in a clockwise direction. When the second winding is energized, the motor moves in a counterclockwise direction. In the preferred embodiment, one motor controls both diverter valves 32, 33. At each limit of the valves' movement, there is a microswitch 232, 234 which senses when the valve limit has been reached.

When one of the microswitches 232, 234 is open, i.e. switch 232, the input to an associated inverter 236 is essentially at ground. When the switch 232 closes, the input to the inverter 236 increases to approximately five volts. After the switch 232 again opens, it takes some time, due to the RC time constant of the associated resistors and capacitor, before the voltage at the input of the first inverter 236 returns to approximately zero. Accordingly, the combination of inverters and the RC network to which each of the switches 232, 234 are connected acts as a switch debouncer. Thus, the output of inverter 238 will be low when switch 232 is closed and high when switch 232 is opened. Similarly, the output of inverter 240 will be low when switch 234 is closed and high when switch 234 is opened.

NAND gate 242 normally has a high output voltage. Accordingly, as will be obvious to those of ordinary skill in the digital circuitry art, LED 106 will be on when switch 232 is closed. Otherwise, LED 106 will be off. Similarly, LED 108 will be on when switch 234 is closed. Note that these LEDs 106, 108 were previously described with reference to the dosimetry controller 62 (See FIG. 3).

When both switches 232, 234 are opened at the same time, there will be two high signals at the input of NAND gate 254. That will cause NAND gate 256 to trigger a monostable multivibrator comprised of one half of a CD4098BE integrated circuit 258 which provides a low going output pulse having a duration of approximately 700 milliseconds in the preferred embodiment of the invention. The particular time period during which this pulse is low must exceed the time period which it would take for the diverter valves 32, 33 to be moved from one position to the other position. In the preferred embodiment of the invention the movement of the diverter valves 32, 33 takes approximately 600 milliseconds. The outputs from the monostable multivibrator are fed via EXCLUSIVE OR gate 260 into a D-type flip-flop 262 comprised of a CD4013BE integrated circuit. In the event that the diverter valves 32, 33 did not move from one position to the other within the prescribed time period, it is presumed that a fault condition occurred, e.g. one of the diverter valves 32, 33 jammed. Accordingly, the operator is advised of the fault condition by both LEDs 106, 108 flashing simultaneously. The flashing occurs as a result of the output of the flip-flop 262 which is connected on line 264 to NAND gate 242 being kept high, thereby causing NAND gate 242 to act as an astable multivibrator which oscillates between high and low outputs thereby causing the EXCLUSIVE OR gates 248, 250 to change states and to flash the LEDs 106, 108.

At the same time that one output of the flip-flop 262 goes high, the other output, on line 266 goes low. The signal on line 266 is normally high, as it is one input to NAND gate 268. The other input to NAND gate 268 is the "End of Elution" signal previously discussed. When both inputs to NAND gate 268 are high the output on line 270 is high. The output signal on line 270 turns off the infusion pump when it is low. This is the signal which remotely controls the infusion pump, as heretofore described. Thus, in the fault condition, when the signal on line 266 goes low the infusion pump is turned off. When there is no fault condition, the infusion pump will be enabled when the End of Elution signal is high.

The "INJECT" line which indicates when the pump is injecting enters the Valve Controller Circuit 230 on line 252. A series of inverters are used to buffer the INJECT signal in order to obtain an output on line 253. The output on line 253 is used as the input to a pair of solid state relays (not shown) which select between the two windings of the motor which drives the diverter valves 32, 33. Thus, when the INJECT line is low the motor drives the diverter valves 32, 33 into the Patient position, and when the INJECT line is high, the motor drives the diverter valves 32, 33 into the Waste position.

I claim:

1. A strontium-rubidium infusion system comprising:
   (a) means for generating rubidium-82 in a solution which can be infused into a patient;
   (b) means for collecting a predefined volume of solution containing rubidium-82;
   (c) means for measuring the radioactivity present in said predefined volume before it is infused into said patient; and
   (d) means for quickly infusing said predefined volume of rubidium-82 into said patient as a single bolus.

2. The strontium-rubidium infusion system of claim 1 wherein said means for generating rubidium-82 in a solution which can be infused into a patient comprises a strontium-rubidium generator.

3. The strontium-rubidium infusion system of claim 2 wherein said means for infusing said solution into a patient comprises a syringe.

4. The strontium-rubidium infusion system of claim 3 wherein said means for infusing said solution into a patient further comprises means for electromechanically operating said syringe.

5. The strontium-rubidium infusion system of claim 4 wherein said means for electromechanically operating said syringe comprises a stepper motor which drives means for moving the plunger of said syringe.

6. The strontium-rubidium infusion system of claim 5 further comprising electronic means for controlling said means for electromechanically operating said syringe comprises a stepper motor which drives means for moving the plunger of said syringe.

7. The strontium-rubidium infusion system of claim 6 further comprising means for measuring the radioactivity present in said solution as it is infused into said patient.

8. The strontium-rubidium infusion system of claim 6 further comprising means for measuring the radioactivity present in said solution as it is infused into said patient.

9. The strontium-rubidium infusion system of claim 6 wherein said means for measuring the radioactivity present in said solution as it is infused into said patient comprises a dosimetry system.

10. The strontium-rubidium infusion system of claim 6 wherein said dosimetry system is connected to means for controlling said means for infusing.

11. The strontium-rubidium infusion system of claim 1 wherein said means for quickly infusing said predefined volume of rubidium-82 into said patient as a single bolus comprises a manually operated wash syringe.

12. The strontium-rubidium infusion system of claim 11 wherein said manually operated wash syringe is initially filled with saline solution.

* * * * *